US009629785B2

(12) United States Patent
Roy et al.

(10) Patent No.: US 9,629,785 B2
(45) Date of Patent: Apr. 25, 2017

(54) PHARMACEUTICAL COMPOSITIONS COMPRISING NANO SIZE DROPLETS OF SKIN WHITENING AGENTS

(75) Inventors: Sunilendu Bhushan Roy, Ahmedabad (IN); Jay Shantilal Kothari, Ahmedabad (IN); Shafiq Sheikh, Ahmedabad (IN); Jitendra Dasharathlal Patel, Ahmedabad (IN); Jinesh Suresh Pancholi, Ahmedabad (IN)

(73) Assignee: CADILA HEALTHCARE LIMITED, Ahmedabad (IN)

( * ) Notice: Subject to any disclaimer, the term of this patent is extended or adjusted under 35 U.S.C. 154(b) by 23 days.

(21) Appl. No.: 13/880,342

(22) PCT Filed: Oct. 18, 2011

(86) PCT No.: PCT/IN2011/000718
§ 371 (c)(1),
(2), (4) Date: Jun. 6, 2013

(87) PCT Pub. No.: WO2012/053009
PCT Pub. Date: Apr. 26, 2012

(65) Prior Publication Data
US 2013/0287825 A1    Oct. 31, 2013

(30) Foreign Application Priority Data
Oct. 21, 2010 (IN) .......................... 2934/MUM/2010

(51) Int. Cl.
| | | |
|---|---|---|
| *A61Q 9/02* | (2006.01) | |
| *A61K 8/06* | (2006.01) | |
| *A61K 8/34* | (2006.01) | |
| *A61K 8/35* | (2006.01) | |
| *A61K 8/362* | (2006.01) | |
| *A61K 8/365* | (2006.01) | |
| *A61K 8/49* | (2006.01) | |
| *A61K 8/63* | (2006.01) | |
| *A61K 8/67* | (2006.01) | |
| *A61Q 19/02* | (2006.01) | |
| *A61K 8/36* | (2006.01) | |

(52) U.S. Cl.
CPC ............... *A61K 8/06* (2013.01); *A61K 8/347* (2013.01); *A61K 8/355* (2013.01); *A61K 8/361* (2013.01); *A61K 8/362* (2013.01); *A61K 8/365* (2013.01); *A61K 8/4946* (2013.01); *A61K 8/4973* (2013.01); *A61K 8/63* (2013.01); *A61K 8/671* (2013.01); *A61K 8/675* (2013.01); *A61Q 19/02* (2013.01); *A61K 2800/20* (2013.01); *A61K 2800/21* (2013.01); *A61K 2800/413* (2013.01); *Y10S 977/773* (2013.01); *Y10S 977/906* (2013.01)

(58) Field of Classification Search
None
See application file for complete search history.

(56) References Cited

U.S. PATENT DOCUMENTS

| | | | |
|---|---|---|---|
| 4,847,074 A | 7/1989 | Hatae et al. | |
| 5,629,021 A | 5/1997 | Wright | |
| 5,824,327 A | 10/1998 | Whittemore | |
| 6,355,811 B1 * | 3/2002 | Kim et al. | 549/408 |
| 6,514,538 B1 | 2/2003 | Ota et al. | |
| 2003/0235540 A1 * | 12/2003 | Herzog | A61K 8/044 424/59 |
| 2004/0081668 A1 | 4/2004 | Puglia | |
| 2005/0271608 A1 * | 12/2005 | Gupta | 424/62 |
| 2008/0299159 A1 * | 12/2008 | Aimi et al. | 424/401 |
| 2010/0119560 A1 * | 5/2010 | Kim et al. | 424/401 |

FOREIGN PATENT DOCUMENTS

| | | |
|---|---|---|
| EP | 443413 A1 | 8/1991 |
| EP | 506197 B1 | 6/1998 |
| EP | 671903 B1 | 12/2001 |
| KR | 20100018118 A | 2/2010 |
| WO | 02055047 A1 | 7/2002 |
| WO | 2004066973 A1 | 8/2004 |
| WO | 2006028339 A1 | 3/2006 |

OTHER PUBLICATIONS

KV Godse. "Triple Combination of Hydroquinone, Tretinoin and Mometasone Furoate With Glycolic Acid Peels in Melasma" (Pubmed Pre-publication). Indian Journal of Dermatology, vol. 54(1), Jan.-Mar. 2009, PMC2800888, 3 printed pages.*
ICI Americas Inc. "The HLB System a time saving guide to emulsifier selection." ICI Americas Inc. Wilmington, Delaware. Revised, Mar. 1980, pp. 1-22.*
JW So, S Kim, JS Park, BH Kim, SH Jung, SC Shin, CW Cho. "Preparation and evaluation of solid lipid nanoparticles with JSH18 for skin-whitening efficacy." Pharmaceutical Development and Technology, vol. 15(4), 2010, pp. 415-420.*
Kiranv Godse; "Triple Combination of Hydroquinone, tretinoin and mometasone furoate with glycolic acid peels in melasma", Indian Journal of Dermatology, vol. 54, No. 1, Jan. 1, 2009, p. 92.
European Patent Office Acting as the International Search Authority; International Search Report; PCT/IN2011/000718; Apr. 26, 2012.

* cited by examiner

*Primary Examiner* — Isaac Shomer
(74) *Attorney, Agent, or Firm* — IPHorgan Ltd.

(57) ABSTRACT

The present invention relates to pharmaceutical compositions comprising mono size droplets of skin whitening agents or salts thereof. In particular, the present invention relates to a stable pharmaceutical composition comprising skin whitening agents or salts thereof along with other pharmaceutically acceptable excipients which possess substantially improved skin whitening effects and also exhibits greater skin permeability. The invention also relates to processes for the preparation of such compositions.

15 Claims, No Drawings

PHARMACEUTICAL COMPOSITIONS COMPRISING NANO SIZE DROPLETS OF SKIN WHITENING AGENTS

FIELD OF THE INVENTION

The present invention relates to pharmaceutical compositions comprising skin whitening agents or salts thereof. In particular, the present invention relates to a stable pharmaceutical composition comprising skin whitening agents or salts thereof along with other pharmaceutically acceptable excipients which possess substantially improved skin whitening effects and also exhibits greater skin permeability. The invention also relates to processes for the preparation of such compositions.

BACKGROUND OF THE INVENTION

A spot, freckle, and pigmentation after skin is exposed to the sun refer to a condition in which melanogenesis is sharply accelerated by activation of pigment cells (melanocyte) which exists in the skin. There has been known a skin external preparation (especially skin-whitening agent) to prevent or ameliorate such skin pigment troubles containing ascorbic acids, hydrogen peroxide, colloidal sulfur, glutathione, hydroquinone, or catechol. However, it is also known that such whitening agents sometimes effectively exert their actions but sometimes do not exert the actions the reason for which may be attributed to poor skin penetration of the applied products.

Conventionally, the skin whitening is tried by mixing material having inhibition function against tyrosinase such as hydroquinone, ascorbic acid, kojic acid, or glutathione with cosmetic such as essence or ointment for external use. However, although hydroquinone shows a prescribed effect of whitening, the mixture amount of the same should be restricted to minimum since the same may seriously irritate the skin or may cause allergic problems. In case of ascorbic acid, since the same is easy to be oxidized, cosmetic mixed with the same has problems of discoloration and change of scent, and in case of kojic acid, the same is restricted to be used since the same is unstable. Further, thiol compound such as glutathione or cysteine has a peculiar bad smell and low absorptiveness to skin.

U.S. Pat. No. 6,514,538 discloses a skin whitening method comprising applying a whitening endermic liniment onto skin, said whitening endermic liniment comprising an extract from a plant of the Solanaceae family (Solanaceae), genus *Withania* (*Withania*), wherein application of said liniment upon skin causes suppression of tyrosinase activity and melanin production therein.

U.S. Pat. No. 5,824,327 discloses a skin whitening cosmetic composition and in particular to such a composition which is anhydrous and incorporates kojic dipalmitate.

U.S. Pat. No. 4,847,074 discloses a kojic acid containing whitener cosmetic composition that includes cyclodextrins for improved stability, i.e. to compensate for color changes.

PCT publication No. WO 2002/055047 discloses a skin whitening compositions comprising arbutin and glucosidase.

U.S. Pat. No. 5,629,021 relates to micellar nanoparticles and methods of their production.

EP Patent No. EP 506197 B1 discloses an aqueous suspension of solid lipid nanoparticles for topical use.

EP Patent No. EP 671903 B1 discloses topical compositions in the form of submicron oil spheres.

Most of the topical preparations contain vehicles comprising permeation enhancers, solvents, and high amount of surfactants to achieve these goals. But use of these agents is harmful, especially in chronic application, as many of them are irritants.

Therefore, despite of the wide availability of products for skin whitening, there exists a need to develop topical preparations which does not involve use of such agents as described above to facilitate drug permeation through the skin, improved onsite delivery and reduced skin irritation.

The compositions of the invention overcome all the commonly encountered problems as exemplified above.

SUMMARY OF THE INVENTION

In one general aspect there is provided a stable topical pharmaceutical composition comprising nano size droplets of one or more skin whitening agents or salts thereof.

In another general aspect there is provided a stable topical pharmaceutical composition comprising nano size droplets of tretinoin or salts thereof.

In another general aspect there is provided a stable topical pharmaceutical composition comprising nano size droplets of tretinoin and hydroquinone or salts thereof.

In another general aspect there is provided a stable topical pharmaceutical composition comprising nano size droplets of tretinoin, hydroquinone, and allantoin or salts thereof.

In another general aspect there is provided a stable topical pharmaceutical composition comprising nano size droplets of one or more skin whitening agents and one or more corticosteroids or salts thereof.

In another general aspect there is provided a stable topical pharmaceutical composition comprising triple combination of hydroquinone, tretinoin and mometasone or salts thereof, wherein at least one of the hydroquinone, tretinoin and mometasone are present in the form of nano size droplets.

In another general aspect there is provided a stable topical pharmaceutical composition comprising nano size droplets of tretinoin or salts thereof, wherein the amount of tretinoin or salt thereof in the composition ranges from about 0.01% to about 0.5% w/w of the composition.

In another general aspect there is provided a stable topical pharmaceutical composition comprising nano size droplets of tretinoin and hydroquinone or salts thereof, wherein the amount of tretinoin or salt thereof in the composition ranges from about 0.01% to about 0.1% w/w and the amount of hydroquinone or salt thereof in the composition ranges from about 0.5% to about 3.0% w/w of the composition.

In another general aspect there is provided a stable topical pharmaceutical composition comprising nano size droplets of tretinoin, hydroquinone, and mometasone or salts thereof, wherein the amount of tretinoin or salt thereof in the composition ranges from about 0.01% to about 0.1% w/w, the amount of hydroquinone or salt thereof in the composition ranges from about 0.5% to about 3.0% w/w, and the amount of mometasone or salt thereof in the composition ranges from about 0.01% to about 0.5% w/w of the composition.

In another general aspect there is provided a stable topical pharmaceutical composition comprising nano size droplets of tretinoin, hydroquinone, and allantoin or salts thereof, wherein the amount of tretinoin or salt thereof in the composition ranges from about 0.01% to about 0.1% w/w, the amount of hydroquinone or salt thereof in the composition ranges from about 0.5% to about 3.0% w/w, and the amount of allantoin or salt thereof in the composition ranges from about 0.5% to about 3.0% w/w of the composition.

In another general aspect there is provided a stable topical pharmaceutical composition comprising nano size droplets of one or more skin whitening agents or salts thereof, wherein said composition comprises oil in amount ranging from about 5 to about 25% w/w of the composition.

In another general aspect there is provided a stable topical pharmaceutical composition comprising nano size droplets of one or more skin whitening agents or salts thereof, wherein said composition comprises one or more emulsifier/s in amount ranging from about 0.1 to about 10% w/w of the composition.

In another general aspect there is provided a stable topical pharmaceutical composition comprising nano size droplets of one or more skin whitening agents or salts thereof, wherein said composition comprises one or more emulsifier/s and oil in the weight ratio ranging from about 0.1:20 to about 0.1:1.

Embodiments of the stable topical pharmaceutical composition may include one or more of the following features. The pharmaceutical composition may further include one or more pharmaceutically acceptable excipients. For example, the pharmaceutically acceptable excipients may include one or more of oils, lipids, stabilizers, emulsifiers, pH adjusting agents, emollients, humectants, preservatives, stabilizers, antioxidants, chelating agents, initiators, thickening agents, and the like.

In another general aspect there is provided a stable topical pharmaceutical composition comprising nano size droplets of one or more skin whitening agents or salts thereof, characterized in that said composition exhibits enhanced therapeutic activity.

In another general aspect there is provided a stable topical pharmaceutical composition comprising nano size droplets of one or more skin whitening agents or salts thereof, wherein the composition retains at least 80% potency of skin whitening agents or salts thereof after storage for 3 months at 40° C. and 75% relative humidity.

Embodiments of the stable topical pharmaceutical composition may include one or more of the following features. The pharmaceutical composition may further include one or more pharmaceutically acceptable excipients. For example, the pharmaceutically acceptable excipients may include one or more of oils, lipids, stabilizers, emulsifiers, pH adjusting agents, emollients, humectants, preservatives, stabilizers, antioxidants, chelating agents, initiators, thickening agents, and the like.

$D_{90}$ particle size of droplets of skin whitening agent or salts thereof in the compositions of the invention is less than about 500 nm, preferable less than about 250 nm and most preferably less than about 100 nm.

In another general aspect there is provided a stable topical pharmaceutical composition prepared by the process comprising:
 a) combining an oily phase comprising one or more skin whitening agents or salts thereof along with other pharmaceutically acceptable excipients with an aqueous phase to form an emulsion;
 b) reducing the particle size of emulsion of step a) to a droplet size having $D_{90}$ particle size of less than 500 nm; and
 c) mixing other pharmaceutically acceptable excipients to the emulsion obtained in step b) and converting it into a suitable finished dosage form.

In another general aspect there is provided a method to whiten the skin comprising administering a stable topical pharmaceutical composition comprising nano size droplets of one or more skin whitening agents or salts thereof.

Embodiments of the stable topical pharmaceutical composition may include one or more of the following features. The pharmaceutical composition may further include one or more pharmaceutically acceptable excipients. For example, the pharmaceutically acceptable excipients may include one or more of oils, lipids, stabilizers, emulsifiers, pH adjusting agents, emollients, humectants, preservatives, stabilizers, antioxidants, chelating agents, initiators, thickening agents, and the like.

The details of one or more embodiments of the invention are set forth in the description below. Other features, objects and advantages of the invention will be apparent from the description and claims.

DETAILED DESCRIPTION OF THE INVENTION

The inventors of the invention have surprisingly found that when skin whitening agents or salts thereof are formulated into nano size droplets in pharmaceutically acceptable emulgel (emulsion gel) system which includes optimized ratios of oils and/or emulsifiers, the composition exhibits enhanced therapeutic effect and also the composition exhibits excellent storage stability. Further, such compositions have enhanced onsite delivery of skin whitening agents and also well tolerated (both locally and systemically).

Moreover, the composition of the invention results in immediate and sustained action and covers large surface area with less quantity and good spreadability, non-irritant to skin and mucous membranes, reduced frequency of application leading to improved patient compliance and offers cosmetic benefits like non-stickiness, and non-greasy feel.

The embodiments of the present invention relates to a stable pharmaceutical composition comprising nano size droplets of one or more skin whitening agents or salts thereof.

In a preferred embodiment, the nano size droplets of skin whitening agents or salts thereof posses a $D_{90}$ particle size of less than about 500 nm.

In a preferred embodiment, the nano size droplets of skin whitening agents or salts thereof posses a $D_{90}$ particle size of less than about 400 nm.

In a preferred embodiment, the nano size droplets of skin whitening agents or salts thereof posses a $D_{90}$ particle size of less than about 300 nm.

In a preferred embodiment, the nano size droplets of skin whitening agents or salts thereof posses a $D_{90}$ particle size of less than about 200 nm.

In a preferred embodiment, the nano size droplets of skin whitening agents or salts thereof posses a $D_{90}$ particle size of less than about 100 nm.

In a further embodiment, the composition of the present invention is stable and retains at least 80% potency of skin whitening agent when stored for at least three months at 40° C. and 75% relative humidity.

In a yet another embodiment, the topical pharmaceutical composition exhibits excellent local and systemic tolerability to skin whitening agents when administered in the form of nano sized droplets.

Skin whitening agent for the purpose of the present invention may be selected from, but not limited to Tretinoin, Hydroquinone, Allantoin, Monobenzyl ether of hydroquinone, Azelaic acid, Kojic acid, Glycolic acid, Mequinol, Retinoids, Niacinamide, Arbutin, or salts thereof.

In a preferred embodiment, the composition comprises nano size droplets of tretinoin or salts thereof.

In a further preferred embodiment, the composition comprises a combination of at least two skin whitening agents or salts thereof.

In an embodiment the composition comprises a combination of tretinoin and hydroquinone or salts thereof.

In a further embodiment the composition comprises a combination of tretinoin, hydroquinone, and allantoin or salts thereof.

In a further embodiment the composition comprises a combination of tretinoin, hydroquinone, and mometasone or salts thereof.

In a further embodiment, the composition comprises about 0.5% to about 5.0% w/w of tretinoin or salt thereof (based on 100% total weight of the composition).

In a further embodiment, the composition comprises about 0.01% to about 0.1% w/w of tretinoin or salt thereof and about 0.5% to about 3.0% w/w of hydroquinone or salt thereof (based on 100% total weight of the composition).

In a further embodiment, the composition comprises about 0.01% to about 0.1% w/w of tretinoin or salt thereof, about 0.5% to about 3.0% w/w of hydroquinone or salt thereof, and about 0.01% to about 0.5% w/w of mometasone or salt thereof (based on 100% total weight of the composition).

In a further embodiment, the composition comprises about 0.01% to about 0.1% w/w of tretinoin or salt thereof, about 0.5% to about 3.0% w/w of hydroquinone or salt thereof, and about 0.5% to about 3.0% w/w of allantoin or salt thereof (based on 100% total weight of the composition).

The composition of the present invention further comprises one or more pharmaceutically acceptable excipients selected from, but not limited to lipids, oils, emulsifiers, stabilizers, initiators, pH adjusting agents, emollients, humectants, preservatives, antioxidants and chelating agents.

Suitable lipids which can be used include one or more of hydrocarbons, fatty alcohols, fatty acids, glycerides or esters of fatty acids with $C_1$-$C_{36}$ alkanols. Hydrocarbons may include paraffin or petroleum jelly. Fatty alcohols may include decanol, dodecanol, tetradecanol, hexadecanol or octadecanol. Fatty acids may include $C_6$-$C_{24}$ alkanoic acids such as hexanoic acid, octanoic acid, decanoic acid, dodecanoic acid, tetradecanoic acid, hexadecanoic acid, octadecanoic acid, unsaturated fatty acids such as oleic acid and linoleic acid. Glycerides may include olive oil, castor oil, sesame oil, caprylic/capric acid triglyceride or glycerol mono-, di- and tri-esters with palmitic and/or stearic acid. Esters of fatty acids may include $C_1$-$C_{36}$ alkanols such as beeswax, carnauba wax, cetyl palmitate, lanolin, isopropyl myristate, isopropyl stearate, oleic acid decyl ester, ethyl oleate and $C_6$-$C_{12}$ alkanoic acid esters and the like.

Suitable oils may include one or more of almond oil, apricot seed oil, borage oil, canola oil, coconut oil, corn oil, cotton seed oil, fish oil, jojoba bean oil, lard oil, linseed oil, boiled macadamia nut oil, mineral oil, olive oil, peanut oil, safflower oil, sesame oil, soybean oil, squalane, sunflower seed oil, tricaprylin (1,2,3 trioctanoyl glycerol) and wheat germ oil and the like. The preferred quantity of oil used is in the range of about 5 to about 25% w/w, and more preferably in the range of about 5% to about 20% w/w of the composition.

Suitable emulsifiers may include one or more of ionic polysorbate surfactant, Tween® 20, Tween® 40, Tween® 60, Tween® 80, Nonylphenol Polyethylene Glycol Ethers, (alkylphenol-hydroxypolyoxyethylene), Poly(oxy-1,2-ethanediyl), alpha-(4-nonylphenol)-omega-hydroxy-, branched (i.e. Tergitol® NP-40 Surfactant), Nonylphenol Polyethylene Glycol Ether mixtures (i.e. Tergitol® NP-70 (70% AQ) Surfactant), phenoxypolyethoxyethanols and polymers thereof such as Triton®, Poloxamer®, Spans®, Tyloxapol®, different grades of Brij, sodium dodecyl sulfate and the like. The preferred quantity of the emulsifiers used is in the range of about 0.1% to about 10% w/w of the composition.

In a preferred embodiment, the ratio of emulsifier or surfactant to oil in the pharmaceutical composition of the present invention ranges from about 0.1:20 to about 0.1:1, preferably about 0.1:10 to about 0.1:1.

Suitable pH adjusting agents which can be used include one or more of organic or inorganic acids and bases including sodium hydroxide, potassium hydroxide, ammonium hydroxide, phosphate buffers, citric acid, acetic acid, fumaric acid, hydrochloric acid, malic acid, nitric acid, phosphoric acid, propionic acid, sulfuric acid, tartaric acid and the like. In an embodiment, the pH of the composition of the invention may range from about 4.5 to about 7.0, and preferably from 5.0 to about 6.5.

Suitable emollients which can be used include one or more of caprylic/capric triglyerides, castor oil, ceteareth-20, ceteareth-30, cetearyl alcohol, ceteth 20, cetostearyl alcohol, cetyl alcohol, cetyl stearyl alcohol, cocoa butter, diisopropyl adipate, glycerin, glyceryl monooleate, glyceryl monostearate, glyceryl stearate, isopropyl myristate, isopropyl palmitate, lanolin, lanolin alcohol, hydrogenated lanolin, liquid paraffins, linoleic acid, mineral oil, oleic acid, white petrolatum, polyethylene glycol, polyoxyethylene glycol fatty alcohol ethers, polyoxypropylene 15-stearyl ether, propylene glycol stearate, squalane, steareth-2 or -100, stearic acid, stearyl alcohol, urea and the like.

Suitable preservatives which can be used include one or more of phenoxyethanol, parabens (such as methylparaben and propylparaben), propylene glycols, sorbates, urea derivatives (such as diazolindinyl urea), and the like.

Suitable antioxidants which can be used include one or more of ascorbic acid, alpha-tocopherol (vitamin-E), butylated hydroxyanisole, butylated hydroxytoluene, glutathione, sodium metabisulphite and the like. The amount of antioxidant may range from about 0.05% to about 1.0% w/w of the total weight of the composition.

Suitable humectants which can be used include one or more of propylene glycol, glycerin, butylene glycol, sorbitol, triacetin and the like.

Suitable chelating agents which can be used include one or more of disodium EDTA, edetate trisodium, edetate tetrasodium, diethyleneamine pentaacetate and the like. The amount of chelating agent may range from about 0.05% to about 0.5% w/w of the total weight of the composition.

Suitable stabilizers may include one or more of ionic polysorbate surfactant, Tween® 20, Tween® 40, Tween® 60, Tween® 80, Nonylphenol Polyethylene Glycol Ethers, (alkylphenol-hydroxypolyoxyethylene), Poly(oxy-1,2-ethanediyl), alpha-(4-nonylphenol)-omega-hydroxy-, branched (i.e. Tergitol® NP-40 Surfactant), Nonylphenol Polyethylene Glycol Ether mixtures (i.e. Tergitol® NP-70 (70% AQ) Surfactant), phenoxypolyethoxyethanols and polymers thereof such as Triton®, Poloxamer®, Spans®, Tyloxapol®, different grades of Brij, sodium dodecyl sulfate and the like. The preferred quantity of the stabilizer or surfactant used is in the range of 1 to 10% w/w of the composition.

Suitable initiators which can be used include one or more of alcohols like $C_1$-$C_{12}$ alcohols, diols and triols, glycerol, methanol, ethanol, propanol, octanol and the like. The amount of initiator may range from about 5.0% to about 9.0% w/w of the total weight of the composition.

The composition of the invention may be prepared by a) combining an oily phase comprising one or more skin whitening agents or salts thereof along with other pharmaceutically acceptable excipients with an aqueous phase to form an emulsion; b) reducing the particle size of emulsion of step a) to a droplet size having $D_{90}$ particle size of 500 nm; and c) mixing other pharmaceutically acceptable excipients to emulsion obtained in step b) and converting it into a suitable finished dosage form.

In an embodiment, the process of preparing the stable pharmaceutical composition comprising nano size droplets of one or more skin whitening agents or salts thereof comprising:

a) preparing a hydroalcoholic phase of one or more skin whitening agents with one or more alcohol, emulsifier and thickening agent.

b) mixing the above hydroalcoholic phase was mixed with one or more oil and water.

c) homogenizing the blend of step (b) to reduce the droplet size to $D_{90}$ particle size of less than 500 nm to form a nano emulsion; and optionally adding the aqueous dispersion of thickening agent to the above nano emulsion to get the nanogel.

The nano size droplets may be produced with reciprocating syringe instrumentation, continuous flow instrumentation, high speed mixing or high pressure homogenization. However, it will appreciated to the person skilled in the art any known method of reducing the size of droplet may be adopted to serve the purpose of the present invention.

Small droplets of the nano emulsion may be formed by passing the emulsion through a homogeniser under different pressures ranging from 3,500-21,500 psi. The emulsion may be passed between 4-5 times under the same conditions to get a final $D_{90}$ droplet size of about 500 nm. The nano droplets formed may be filtered through 0.2 to 0.4 micron filter.

The gel base may be used in the present invention to form a gel matrix for the preparation of nanogel from nanoemulsion. The gel base comprises of one or more of thickening agents.

Suitable thickening agents may include one or more of cellulose polymer, a carbomer polymer, a carbomer derivative, a cellulose derivative, polyvinyl alcohol, poloxamers, polysaccharides and the like.

Suitable dosage form of the invention may include cream, gel, ointment, lotion, spray, foam and emulsion.

In a preferred embodiment, the composition of the invention is in the form of gel.

The present invention further provides a method to whiten the skin comprising administering a stable topical pharmaceutical composition comprising nano size droplets of one or more skin whitening agents or salts thereof.

The invention is further illustrated by the following examples which are provided to be exemplary of the invention and do not limit the scope of the invention. While the present invention has been described in terms of its specific embodiments, certain modifications and equivalents will be apparent to those skilled in the art and are intended to be included within the scope of the present invention.

Example 1: Hydroquinione, Tretinoin and Mometasone Furoate Nanogel

TABLE 1

| Ingredients | Formula 1 % w/w | Formula 2 % w/w |
|---|---|---|
| Hydroquinone | 1-3 | 1-3 |
| Tretinoin | 0.01-0.1 | 0.01-0.1 |
| Mometasone Furoate | 0.1 | 0.1 |
| Alcohol | 5-9 | 5-9 |
| Tween 20 | 1-5 | 1-5 |
| Soyabean Oil | 7-11 | 7-11 |
| Propylene Glycol | 3-7 | 3-7 |
| Ascorbic Acid | 0.05-0.5 | 0.05-0.5 |
| Disodium EDTA | 0.05-0.5 | 0.05-0.5 |
| Sodium Metabisulphite | 0.05-0.5 | 0.05-0.5 |
| Carbopol 980 NF | 0.5-2.0 | 0.5-2.0 |
| Sodium Hydroxide | Q.S | Q.S |
| Purified Water | Q.S | Q.S |

Procedure:

Hydroquinone and Tretinoin were dissolved in alcohol, Polysorbate 20 and Propylene Glycol. This hydroalcoholic phase was mixed with soyabean oil and aqueous solution of ascorbic acid. The resulting blend was homogenized to reduce the droplet size to $D_{90}$ particle size of about 250 nm by high pressure homogenization to form the nano-emulsion. Mometasone Furoate and Sodium Metabisulphite were added to the aqueous dispersion of Carbomer. Desired pH was then adjusted by addition of Sodium Hydroxide solution. The aqueous dispersion of carbomer was then mixed with the nano-emulsion to form a nanogel.

Example 2: Hydroquinione, Tretinoin and Mometasone Furoate Nanogel

TABLE 2

| Ingredients | % w/w |
|---|---|
| Hydroquinione | 0.5-3 |
| Tretinoin | 0.01-0.1 |
| Mometasone Furoate | 0.01-0.5 |
| Alcohol | 6-9 |
| Tween 20 | 3-7 |
| Soyabean Oil | 7-11 |
| Propylene glycol | 6-9 |
| Ascorbic Acid | 0.05-0.5 |
| Disodium EDTA | 0.05-0.5 |
| Sodium Metabisulphite | 0.1-0.5 |
| Ultrez 10NF | 0.5-2 |
| Sodium Hydroxide | Q.S |
| Purified Water | Q.S |

Procedure

Hydroquinone and Tretinoin were dissolved in alcohol, Polysorbate 20 and Propylene Glycol. This hydroalcoholic phase was mixed with soyabean oil under stirring. Aqueous solution of ascorbic acid was then added to the above mixture. The resulting blend was homogenized to reduce the droplet size to $D_{90}$ particle size of about 250 nm by high pressure homogenization to get the nano-emulsion. Mometasone Furoate and Sodium Metabisulphite were added to the aqueous dispersion of Ultrez 10. Desired pH was adjusted by addition of Sodium Hydroxide solution. The above aqueous dispersion of Ultrez 10 was then mixed with nano-emulsion to form a nanogel.

Example 3: Hydroquinione, Tretinoin and Allantoin Nanogel

TABLE 3

| Ingredients | % w/w |
| --- | --- |
| Hydroquinione | 0.5-3 |
| Tretinoin | 0.01-0.1 |
| Allantoin | 0.25-2 |
| Alcohol | 6-9 |
| Tween 20 | 1-5 |
| Soyabean Oil | 7-11 |
| Propylene Glycol | 3-7 |
| Ascorbic Acid | 0.25-2 |
| Disodium EDTA | 0.25-2 |
| Sodium Metabisulphite | 0.01-0.5 |
| Carbopol 980 | 0.5-2 |
| Sodium Hydroxide | Q.S |
| Purified Water | Q.S |

Procedure:

Hydroquinone and Tretinoin were dissolved in alcohol, Polysorbate 20 and Propylene Glycol. This hydroalcoholic phase was mixed with soyabean oil under stirring. Aqueous solution of ascorbic acid was then added to the above mixture. The resulting blend was homogenized to reduce the droplet size to $D_{90}$ particle size of about 250 nm by high pressure homogenization to get the nano-emulsion. Allantoin and Sodium Metabisulphite were added to the aqueous dispersion of Carbopol. Desired pH was adjusted by addition of Sodium Hydroxide solution. The above aqueous dispersion of Carbopol was then mixed with nano-emulsion to form a nanogel.

Example 4: Hydroquinione, Tretinoin and Allantoin Nanogel

TABLE 4

| Ingredients | % w/w |
| --- | --- |
| Hydroquinione | 0.5-3 |
| Tretinoin | 0.01-0.1 |
| Allantoin | 0.5-3 |
| Alcohol | 6-9 |
| Tween 20 | 3-6 |
| Soyabean Oil | 7-10 |
| Propylene Glycol | 3-6 |
| Citric Acid Monohydrate | 0.01-0.5 |
| BHT | 0.01-0.5 |
| Di Sodium EDTA | 0.01-0.5 |
| Sodium Metabisulphite | 0.01-0.5 |
| Ultrez 10 | 0.5-3 |
| Perfume | 0.01-0.1 |
| Sodium Hydroxide | Q.S |
| Purified Water | Q.S |

Procedure:

Hydroquinone and Tretinoin were dissolved in alcohol, Polysorbate 20 and Propylene Glycol. This hydroalcoholic phase was mixed with soyabean oil under stirring. Aqueous solution of Citric acid monohydrate was then added to the above mixture. The resulting blend was homogenized to reduce the droplet size to $D_{90}$ particle size of about 250 nm by high pressure homogenization to get the nano-emulsion. Allantoin and Sodium Metabisulphite were added to the aqueous dispersion of Ultrez 10. Desired pH was adjusted by addition of Sodium Hydroxide solution. The above aqueous dispersion of Ultrez 10 was then mixed with nano-emulsion to form a nanogel.

Example 5: Hydroquinione and Tretinoin Nanogel

TABLE 5

| Ingredients | % w/w |
| --- | --- |
| Hydroquinione | 0.5-3 |
| Tretinoin | 0.01-0.1 |
| Alcohol | 5-8 |
| Tween 20 | 3-7 |
| Soyabean Oil | 7-10 |
| Propylene Glycol | 3-7 |
| Citric Acid Monohydrate | 0.05-0.5 |
| BHT | 0.05-0.5 |
| Sodium Metabisulphite | 0.05-0.5 |
| Ultrez 10 | 0.5-3 |
| Sodium Hydroxide | Q.S |
| Purified Water | Q.S |

Procedure:

Hydroquinone, Tretinoin & BHT were dissolved in alcohol, Tween 20, Propylene Glycol, soyabean oil and aqueous solution of Citric acid monohydrate. The resulting blend was homogenized to reduce the droplet size to $D_{90}$ particle size of about 250 nm by high pressure homogenization to get the nano-emulsion. Separately, Sodium Metabisulphite was added to the aqueous dispersion of Ultrez 10. Desired pH was adjusted by addition of Sodium Hydroxide solution. The above aqueous dispersion of ULTREZ 10 was then mixed with nano-emulsion to form a Nanogel.

Example 6: Hydroquinione and Tretinoin Nanogel

TABLE 6

| Ingredients | % w/w Composition |
| --- | --- |
| Hydroquinione | 0.5-3 |
| Tretinoin | 0.01-0.5 |
| Alcohol | 6-9 |
| Tween 20 | 3-6 |
| Soyabean Oil | 7-10 |
| Propylene Glycol | 3-7 |
| Citric Acid Monohydrate | 0.05-0.5 |
| BHT | 0.05-0.5 |
| Sodium Metabisulphite | 0.05-0.5 |
| Ultrez 10 | 0.5-3 |
| Sodium Hydroxide | Q.S |
| Purified Water | Q.S |

Procedure:

Hydroquinone, Tretinoin & BHT were dissolved in alcohol, Polysorbate 20 and Propylene Glycol, soyabean oil and aqueous solution of Citric Acid Monohydrate. The resulting blend was homogenized to reduce the droplet size to $D_{90}$ particle size of about 250 nm by high pressure homogenization to get the nano-emulsion. Sodium Metabisulphite was added to the aqueous dispersion of Ultrez 10 and the desired pH was adjusted by addition of Sodium Hydroxide solution. The above aqueous dispersion of Ultrez 10 was then mixed with nano-emulsion to form a nanogel.

Example 7: Hydroquinione, Tretinoin and Mometasone Furoate Nanogel

TABLE 7

| Ingredients | % w/w |
| --- | --- |
| Hydroquinione | 0.5-3 |
| Tretinoin | 0.01-0.1 |
| Alcohol | 5-9 |
| Tween 20 | 3-7 |
| Soyabean Oil | 7-10 |
| Propylene Glycol | 3-7 |
| Citric Acid Monohydrate | 0.05-0.5 |
| BHT | 0.05-0.5 |
| Sodium Metabisulphite | 0.05-0.5 |
| Ultrez 10 | 0.5-3 |
| Mometasone Furoate | 0.05-0.5 |
| Sodium Hydroxide | Q.S |
| Purified Water | Q.S |

Procedure:

Hydroquinone, Tretinoin and BHT were dissolved in alcohol, Tween 20, Propylene Glycol, soyabean oil and aqueous solution of Citric Acid Monohydrate. The resulting blend was homogenized to reduce the droplet size to $D_{90}$ particle size of about 250 nm with the help of high pressure homogenization to get the nano-emulsion. Mometasone Furoate and Sodium Metabisulphite was then added to aqueous dispersion of Carbomer. Desired pH was adjusted by addition of Sodium Hydroxide solution. The above aqueous dispersion of ULTREZ 10 NF was then mixed with nano-emulsion to form a Nanogel.

Example 8: Tretinoin Nanogel

TABLE 8

| Ingredients | % w/w |
| --- | --- |
| Tretinoin | 0.01-0.1 |
| Polysorbate 80 | 1-5 |
| Glycerol | 3-7 |
| Alcohol | 3-7 |
| Soya Oil | 7-11 |
| Disodium EDTA | 0.05-0.5 |
| Carbopol 980 | 0.5-3 |
| Citric Acid Monohydrate | 0.05-0.5 |
| BHT | 0.05-0.5 |
| Sodium Hydroxide | q.s. |
| Purified Water | q.s. |

Procedure:

Tretinoin and BHT were dissolved in alcohol, Polysorbate 80, Glycerol, soyabean oil, disodium EDTA and aqueous solution of Citric Acid Monohydrate. The resulting blend was homogenized to reduce the droplet size to $D_{90}$ particle size of about 250 nm by homogenization to get the nano-emulsion. Sodium hydroxide solution was added to the aqueous dispersion of Carbopol 980 which was then mixed with nano-emulsion to form a nanogel.

Example 9: Tretinoin Nanogel

TABLE 9

| Ingredients | % w/w |
| --- | --- |
| Tretinoin | 0.01-0.5 |
| Polysorbate 80 | 1-5 |
| Glycerol | 3-7 |
| Alcohol | 3-7 |
| Soya Oil | 7-10 |
| Disodium EDTA | 0.05-0.5 |
| Carbopol 980 | 0.5-3 |
| Citric Acid Monohydrate | 0.05-0.5 |
| BHT | 0.05-0.5 |
| Sodium Hydroxide | q.s. |
| Purified Water | q.s. |

Procedure:

Tretinoin and BHT were dissolved in alcohol, Polysorbate 80, Glycerol, soyabean oil and Citric Acid Monohydrate was dissolved in water which was then added to the above mixture. The resulting blend was homogenized to reduce the droplet size to $D_{90}$ particle size of about 250 nm with the help of high pressure homogenization to get the nano-emulsion. Sodium hydroxide solution was added to the aqueous dispersion of Carbopol 980 which was then mixed with nano-emulsion to form a nanogel.

Example 10: Stability Study on Nanogel Composition of Example 1 and 2

TABLE 10

| | % Drug in the formulation | | | |
| --- | --- | --- | --- | --- |
| Drug/Property | Initial | 1 Month | 2 Month | 3 Month |
| Hydroquinone | 100.6 | 98.55 | 99.9 | 100.45 |
| Tretinoin | 98.1 | 94.7 | 98.45 | 95.6 |
| Mometasone | 94.5 | 93.6 | 95.0 | 97.15 |
| pH | 5.56 | 5.3 | 5.47 | 5.72 |

TABLE 11

| | % Drug in the formulation | | | |
| --- | --- | --- | --- | --- |
| Drug/Property | Initial | 1 Month | 2 Month | 3 Month |
| Hydroquinone | 101.7 | 100.0 | 98.25 | 100.7 |
| Tretinoin | 96.3 | 95.55 | 96.75 | 95.25 |
| Mometasone | 93.8 | 92.0 | 93.65 | 96.25 |
| pH | 5.69 | 5.6 | 5.54 | 5.89 |

Table 10 & 11 provides stability data of nanogel composition of Example 1 & 2 respectively when stored at 40° C. and 75% relative humidity for three months and indicates that said compositions remains stable and retains at least 80% potency of tretinoin, hydroquinone and allantoin over the storage period.

Example 11: Stability Study on Nanogel Composition of Example 3 and 4

TABLE 12

| | % Drug in the formulation | | | |
| --- | --- | --- | --- | --- |
| Drug/Property | Initial | 1 Month | 2 Month | 3 Month |
| Hydroquinone | 103.1 | 100.25 | 100.05 | 100 |
| Tretinoin | 99.7 | 96.05 | 97.5 | 94.6 |

TABLE 12-continued

| | % Drug in the formulation | | | |
|---|---|---|---|---|
| Drug/Property | Initial | 1 Month | 2 Month | 3 Month |
| Allantoin | 100.75 | 100.5 | 95.7 | 100.6 |
| pH | 5.51 | 5.3 | 5.31 | 5.79 |

TABLE 13

| | % Drug in the formulation | | | |
|---|---|---|---|---|
| Drug/Property | Initial | 1 Month | 2 Month | 3 Month |
| Hydroquinone | 103.2 | 100.6 | 98.6 | 99.85 |
| Tretinoin | 100.55 | 96.8 | 97.75 | 94.45 |
| Allantoin | 101.1 | 101.8 | 98.6 | 94.6 |
| pH | 5.55 | 5.3 | 5.29 | 5.96 |

Table 12 & 13 provides stability data of nanogel composition of Example 3 & 4 respectively when stored at 40° C. and 75% relative humidity for three months and indicates that said compositions remain stable and retains at least 80% potency of tretinoin, hydroquinone and allantoin over the storage period.

Example 12: Stability Study on Nanogel Composition of Example 5 and 6

TABLE 14

| | % Drug in the formulation | | |
|---|---|---|---|
| Drug/Property | Initial | 1 Month | 2 Month |
| Hydroquinone | 96.6 | 98.4 | 98.6 |
| Tretinoin | 94.0 | 97.1 | 97.0 |
| pH | 6.30 | 6.91 | 6.82 |

TABLE 15

| | % Drug in the formulation | | |
|---|---|---|---|
| Drug/Property | Initial | 1 Month | 2 Month |
| Hydroquinone | 101.6 | 99.0 | 102.6 |
| Tretinoin | 96.8 | 99.0 | 99.4 |
| pH | 5.24 | 6.93 | 6.82 |

Table 14 & 15 provides stability data of nanogel composition of Example 5 & 6 respectively when stored at 40° C. and 75% relative humidity for three months and indicates that said compositions remains stable and retains at least 80% potency of tretinoin, hydroquinone and allantoin over the storage period.

While the invention has been described in terms of its specific embodiments, certain modifications and equivalents will be apparent to those skilled in the art and are intended to be included within the scope of the invention.

We claim:

1. A stable topical skin-whitening nanogel pharmaceutical composition comprising one or more skin whitening agents or salts thereof, the nanogel composition comprising a nanoemulsion and a gel base, the nanoemulsion comprising nano size droplets of one or more skin whitening agents or salts thereof, 0.1% to 10% w/w emulsifiers, 5% to 25% w/w of oils/lipids, and one or more pharmaceutically acceptable excipients,
wherein the gel base comprises one or more thickening agents, and
wherein the one or more pharmaceutically acceptable excipients are selected from the group consisting of initiators, pH adjusting agents, emollients, humectants, preservatives, antioxidants, and chelating agents, and
wherein the nanogel composition retains at least 80% potency of said skin whitening agent or salts thereof after storage for 3 months at 40° C. and 75% relative humidity.

2. The stable topical pharmaceutical composition of claim 1, wherein the nano size droplets of skin whitening agent or salts thereof have a $D_{90}$ particle size of about 500 nm or less.

3. The stable topical pharmaceutical composition of claim 2, wherein the nano size droplets of skin whitening agent or salts thereof have a $D_{90}$ particle size of about 300 nm or less.

4. The stable topical pharmaceutical composition of claim 2, wherein the nano size droplets of skin whitening agent or salts thereof have a $D_{90}$ particle size of about 100 nm or less.

5. The stable topical pharmaceutical composition of claim 1, wherein the skin whitening agent comprises one or more of Tretinoin, Hydroquinone, Allantoin, Monobenzyl ether of hydroquinone, Azelaic acid, Kojic acid, Mequinol, Niacinamide, Arbutin, or salts thereof.

6. The stable topical pharmaceutical composition of claim 5, wherein the skin whitening agent comprises tretinoin or salts thereof.

7. The stable topical pharmaceutical composition of claim 5, wherein the skin whitening agent comprises tretinoin or salts thereof and hydroquinone or salts thereof.

8. The stable topical pharmaceutical composition of claim 5, wherein the skin whitening agent comprises tretinoin or salts thereof, hydroquinone or salts thereof, and allantoin or salts thereof.

9. The stable topical pharmaceutical composition of claim 1, wherein the composition further comprises one or more corticosteroids or salts thereof.

10. The stable topical pharmaceutical composition of claim 7, wherein the composition further comprises mometasone, salts thereof, or mometasone furoate.

11. The stable topical pharmaceutical composition of claim 1, wherein the emulsifier is selected from the group consisting of ionic polysorbate surfactant, Nonylphenol Polyethylene Glycol Ethers, alkylphenol-hydroxypolyoxyethylene, Poly(oxy-1,2-ethanediyl), alpha-(4-nonylphenol)-omega-hydroxy-, branched, Nonylphenol Polyethylene Glycol Ether mixtures, phenoxypolyethoxyethanols and polymers thereof, Polyoxyethylene glycol alkyl ethers, and sodium dodecyl sulfate.

12. The stable topical pharmaceutical composition of claim 1, wherein the emulsifiers and oils/lipids are present in the composition in a weight ratio of from about 0.1:20 to about 0.1:1.

13. The composition of claim 1, wherein the thickening agents are selected from the group consisting of a carbomer polymer (polyacrylic acid), a cellulose derivative, polyvinyl alcohol, poloxamers, and polysaccharides.

14. A skin-whitening topical nanogel composition comprising:
(a) nano sized droplets comprising about 0.01% to about 0.1% w/w of tretinoin, which is a skin whitening agent;
(b) nano sized droplets comprising about 1.0% to about 3.0% w/w of hydroquinone or a salt thereof, which is a skin whitening agent or a salt thereof;
(c) about 0.01% to about 0.5% w/w of mometasone furoate;
(d) about 5.0% to about 9.0% w/w of alcohol;

(e) about 0.1% to about 10.0% w/w of emulsifiers, wherein the emulsifier is selected from the group consisting of ionic polysorbate surfactant, Nonylphenol Polyethylene Glycol Ethers, alkylphenol-hydroxypolyoxyethylene, Poly(oxy-1,2-ethanediyl), alpha-(4-nonylphenol)-omega-hydroxy-, branched, Nonylphenol Polyethylene Glycol Ether mixtures, phenoxypolyethoxyethanols and polymers thereof, Polyoxyethylene glycol alkyl ethers, and sodium dodecyl sulfate;
(f) about 5% to about 25% w/w of oil/lipids;
(g) about 0.05% to about 1.0% w/w of antioxidants;
(h) about 0.05% to about 0.5% w/w of chelating agents;
(i) one or more pH adjusting agents;
(j) a gel base which comprises one or more thickening agents; and
(k) water,
wherein the composition retains at least 80% potency of skin whitening agents or salts thereof after storage for 3 months at 40° C. and 75% relative humidity.

15. A method of making the composition of claim 14 comprising:

(a) dissolving hydroquinone and tretinoin in a solution of alcohol, polysorbate 20, and propylene glycol;

(b) mixing the solution from step (a) with both soyabean oil and an aqueous solution of ascorbic acid;

(c) homogenizing the composition in step (b) to reduce the droplet size by high pressure homogenization to have a $D_{90}$ of less than about 250 nm;

(d) combining mometasone furoate and sodium metabisulphite with an aqueous dispersion of carbomer (polyacrylic acid);

(e) mixing the dispersion of step (d) with the homogenate of step (c) to form a nanogel pharmaceutical composition.

* * * * *